US008580827B2

(12) United States Patent
Chen et al.

(10) Patent No.: US 8,580,827 B2
(45) Date of Patent: Nov. 12, 2013

(54) ANTI-*FRANCISELLA* AGENTS

(75) Inventors: Ching-Shih Chen, Upper Arlington, OH (US); Hao-Chieh Chiu, Columbus, OH (US); Samuel Kulp, Hilliard, OH (US); John S. Gunn, Powell, OH (US); Larry S. Schlesinger, Powell, OH (US)

(73) Assignee: The Ohio State University Research Foundation, Columbus, OH (US)

( * ) Notice: Subject to any disclaimer, the term of this patent is extended or adjusted under 35 U.S.C. 154(b) by 0 days.

(21) Appl. No.: 13/610,967

(22) Filed: Sep. 12, 2012

(65) Prior Publication Data

US 2013/0005788 A1    Jan. 3, 2013

Related U.S. Application Data

(62) Division of application No. 12/428,035, filed on Apr. 22, 2009, now abandoned.

(51) Int. Cl.
*A61K 31/41* (2006.01)
(52) U.S. Cl.
USPC .......................................... 514/359; 514/403
(58) Field of Classification Search
USPC ................................... 514/359, 403
See application file for complete search history.

(56) References Cited

U.S. PATENT DOCUMENTS

| 5,091,387 A | 2/1992 | Evans et al. |
| 5,134,142 A | 7/1992 | Matsuo |
| 5,206,240 A | 4/1993 | Baldwin |
| 5,466,823 A | 11/1995 | Talley |
| 5,521,207 A | 5/1996 | Graneto |
| 5,550,147 A | 8/1996 | Matsuo |
| 5,639,777 A | 6/1997 | Lee |
| 5,670,509 A | 9/1997 | Evans |
| 5,760,068 A | 6/1998 | Talley |
| 5,972,986 A | 10/1999 | Seibert |
| 6,025,353 A | 2/2000 | Masferrer |
| 7,026,346 B2 | 4/2006 | Chen |
| 7,183,306 B2 | 2/2007 | Shirai |
| 7,576,116 B2 | 8/2009 | Chen |
| 8,039,502 B2 * | 10/2011 | Chen et al. .................... 514/406 |
| 2002/0032238 A1 | 3/2002 | Priepke |
| 2003/0162824 A1 | 8/2003 | Krul |
| 2003/0219461 A1 * | 11/2003 | Britten et al. .............. 424/204.1 |
| 2003/0236294 A1 | 12/2003 | Chen |
| 2004/0014749 A1 * | 1/2004 | Michaelis et al. ......... 514/224.5 |
| 2004/0116475 A1 | 6/2004 | Shirai et al. |
| 2006/0079566 A1 | 4/2006 | Chen |
| 2006/0142368 A1 | 6/2006 | Chen |
| 2008/0146815 A1 | 6/2008 | Chen |
| 2008/0269309 A1 | 10/2008 | Chen |

FOREIGN PATENT DOCUMENTS

| EP | 418845 | 3/1991 |
| EP | 431943 | 6/1991 |
| EP | 444945 | 9/1991 |
| EP | 554829 | 8/1993 |
| EP | 1512396 | 3/2005 |
| SG | 120841 | 7/2007 |
| WO | 9515315 | 6/1995 |
| WO | 9641626 | 12/1996 |
| WO | 03086287 | 10/2003 |
| WO | 2005044130 | 5/2005 |
| WO | 2008130669 | 10/2008 |

OTHER PUBLICATIONS

Birmingham, Smith, Bakowski, Yoshimori and Brumell, Autophagy Controls Salmonella Infection in Response to Damage to the Salmonella-Containing Vacuole, The Journal of Biological Chemistry, Apr. 21, 2006, pp. 11374-11383, vol. 281, No. 16.
Masaaki, Kiyoshi,Takashi and Nobukiyo, Preparation of Pyrazole Derivatives with Anti inflammatory, Analgesic, and Antithrombolic Activity, Hcaplus Copyright 2007, 2 pages.
Product Information, Catalog No. 10008005, Cayman Chemical, May 11, 2006, 3 page.
Gutierrez, Master, Singh, Taylor, Columbo and Deretic, Autophagy is a Defense Mechanism Inhibiting BCG and Mycobacterium Tuberculosis Survival in Infected Macrophages, Cell. Dec. 17, 2004, pp. 753-766, vol. 119.
Buchdunger, Zimmerman, Mett, Meyer, Muller, Druker, and Lydon, Inhibition of the Abl Protein-Tyrosine Kinase in Vitro and in Vivo by a 2-Phenylaminopyrimidine Derivative, Cancer Research, Jan. 1, 1996, pp. 100-104.
De Vleeschauwer and Gauthier, Remarkably Mild and Simple Preparations of Sulfinates, Sulfonyl Chlorides and Sulfonamides from Thioanisoles, Synlett, Apr. 1997, pp. 375-377.
Groesch, Tegeder, Niederberger, Braeutigam, and Geisslinger, Cox-2 Independent Induction of Cell Cycle Arrest and Apoptosis in Colon Cancer Cells by the Selective COX-2 Inhibitor Celecoxib, Caplus, 2005, 2 pages.
Johnson, Smith, Jiuxiang, Heerema, Jefferson, Mone, Grever, Chen and Byrd, A Novel Celecoxib Derivative, Induces Cytotoxicity in Primary CLL Cells and Transformed B-cell Lymphoma via a Caspase adn Bcl-2 Independed Mechanism, Blood First Edition Paper, Sep. 28, 2004, 33 pages.

(Continued)

*Primary Examiner* — Sreeni Padmanabhan
*Assistant Examiner* — Shobha Kantamneni
(74) *Attorney, Agent, or Firm* — Tarolli, Sundheim, Covell & Tummino LLP

(57) ABSTRACT

A series of celecoxib derivatives defined by Formula I:

were prepared and evaluated for their ability to inhibit the gram-negative bacteria *Francisella tularensis*. Pharmaceutical compositions including celecoxib derivatives and their use in methods for treating or preventing infection by *Francisella tularensis* in a subject are described.

6 Claims, 4 Drawing Sheets

(56) References Cited

OTHER PUBLICATIONS

Nakagawa, Amano, Mizushima, Yamamoto, Yamaguchi, Kamimoto, Nara, Funao, Nakata, Tsuda, Hamada, and Yoshimori. Autophagy Defends Cells Against Invading Group A Streptoccus, Science Magazine, Nov. 5, 2004, pp. 1037-1040, vol. 306.
Penning, Talley, Bertenshaw, Carter, Collins, Docter, Graneto, Lee, Malecha, Miyashiro, Rogers, Roger, Yu, Anderson, Burton, Cogburn, Gregory, Koboldt, Perkins, Seibert, Veenhuzien, Zhang and Isakson, Synthesis and Biological Evaluation of the 1,5-Diarylpyrazole Class of Cyclooxygenase-2 Inhibitors: Identification of 4-[5-(4-Methylphenyl) 3-(trifluoromethyl)-1H-Pyrazol-1-yl] Benzenesulfonamide (SC-58635, Celecoxib), J. Med Chem. 1997, pp. 1347-1365.
Yacub, Park, Hanna, Hong, Mitchell, Pandya, Harada, Powis, Chen, Koumenis, Grant and Dent, Promotes Capase-Independent but PERK-, Cathepsin B-, BID-, and AIF-Dependent Killing of Transformed Cells, Molecular Pharmacology, Apr. 18, 2006, 3 pages.
Yacub, Park, Hanna, Hong, Mitchell, and Grant, Regulated Cell Growth in Vitro of Human Glioma Cells, Massey Cancer Center, 2 pages.
Zhao, Jiang, Want, Wu, Lee, Yokom, Stratford, Klinge, Chen, Bally, Yapp and Dunn, The Phosphoinositide-Dependent Kinase-1 Inhibitor, Prevents Y-box Binding Protein-1 (YB-1) from Inducing Epidermal Growth Factor Receptor (EGFR), Molecular Pharmacology, Jun. 26, 2007, 48 pages.
Ahlstrom, Ridderstrom, Zamora and Luthman, CYP2C9 Structure-Metabolism Relationships: Optimizing the Metabolic Stability of COX-2 Inhibitors, J. Med Chem., 2007—pp. 444-4452.
Fustero, Roman, Sanz-Cervera, Simon-Fuentes, Cunat, Villanova and Murguia, Improved Regioselectivity in Pyrazole Formation through the Use of Fluorinated Alcohols as Solvents: Synthesis and Biological Activity of Fluorinated Tebufenpyrad Analogs, J. Org. Chem, 2008, pp. 3523-3259.
Chiu, Yang, Soni, Kulp, Gunn, Schlesinger and Chen, Pharmacological Exploitation of an Off-Target Antibacterial Effect of the Cyclooxygenase-2 Inhibitor Celecoxib against *Francisella tularensis*, Antimicrobial Agents and Chemotherapy, Jul. 2009, pp. 2998-3002, vol. 53, No. 7.
Habeeb, Rao and Knaus, Design and Synthesis of Celecoxib and Refecoxib Analogues as Selective Cyclooxygenase-2 (COX-2) Inhibitors: Replacement of Sulfonamide and Methylsulfonyl Pharmacophores by an Azido Bioisostere,, J. Med. Chem, 2001, pp. 3039-3042.
Singh, Vobbalareddy, Shivaramakrishna, Krishanamraju, Rajjak, Casturi, Akhila and Rao, Methanesulfonamide Group at Position-4 of the C-5-Phenyl Ring of 1,5-Diarylpyrazole Affords a Potent Class of Cyclooxygenase-2 (COX-2) Inhibitors, Bioorganic & Medical Chemistry Letters, 2004, pp. 1683-1688.
Sloop, Bumgardner, and Loehle, Synthesis of Fluorinated Heterocycles, Journal of Fluorine Chemistry, 2002, pp. 135-147.
Sosnovskihk, Barabanov and Sizov, 2-Polyfluoroalkylchromones.., Russian Chemical Bulletin, International Edition, Jul. 2002, pp. 1280-1291, vol. 51, No. 7.
Uddin, Rao and Knaus, Design and Synthesis of Novel Celecoxib Analogues as Selective Cyclooxygenase-2 (COX-2) Inhibitors: Replacement of the Sulfonamide Pharmacophore by a Sulfonylazide Bioisostere, Bioorganic & Medicinal Chemistry, 2003, pp. 5273-5280.
Guzman, Diaz, Trejo, and Lopez-Munoz, Synthesis of Potential Anti-Inflammatory Compounds, Selective Inhibitors of Cyclooxygenase-2 (COX-2), CALPUS XP-02595199 2 pages.
Schonthal, Direct Non-Cyclooxygenase-2 Targets of Celecoxib and Their Potential Relevance for Cancer Therapy, British Journal of Cancer, 2007, pp. 1465-1468.
Ran and Mei, Preparation of Diphenyl Pyrazole Derivatives as Anti-Inflammatory Agents and Analgesics, CAPLUS, XP-002595201, 2 pages.
Jenkins, Drug Eluting Coronary Stents, BMJ, Dec. 7, 2002, pp. 1315-1316, vol. 235.
Ding, Han, Zhu, Chen and D'Ambrosio, Celecoxib Derivatives Induce Apoptosis via the Disruption of Mitochondrial Membrane Potential and Activation of Capase 9, Int. J. Cancer, 2005, pp. 803-810.
Tacconelli, Capone, Sciulli, Ricciotti and Patrignani, The Biochemical Selectivity of Novel COX-2 Inhibitors in Whole Blood Assays of COX-Isozyme Activity, Current Medical Research and Opinion, 2002, pp. 503-511, vol. 18, No. 8.
Irache, Salman, Garnazo and Espuelas, Mannose-Targeted Systems for the Delivery of Therapeutics, Informa Healthcare, Expert Opinion Drug Delivery, 2008, pp. 703-724.
Prasit, Wang, Brideau, Chan, Cormlish, Evans, Hutchinson, Gordon, Guay, Gresser, Kennedy, Leblanc, Leger, Mancini, O'Neill, Oullet, Percival, Perrier, Riendeau, Tagari, Vickers, Wong, Xu, Young and Zomboni, The Discovery of Rofecoxib (MK 966, VIOXX 4-(4'-Methylsulfonylphenyl)-3-Phenyl-2 (5H)-Furanone), an Orally Active Cyclooxygenase-2 Inhibitor, Bioorganic & Medicinal Chemistry Letters 9, 1999, pp. 1773-1778.

* cited by examiner

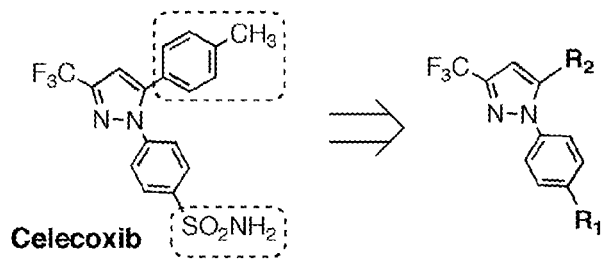

| # | R₁ | R₂ | MIC ($\mu$g/ml) Fn* | MIC ($\mu$g/ml) LVS | # | R₁ | R₂ | MIC ($\mu$g/ml) Fn* | MIC ($\mu$g/ml) LVS |
|---|---|---|---|---|---|---|---|---|---|
| | | Celecoxib | 32 | 16 | 11 | SO$_2$NH$_2$ | -C₆H₄-C₆H₄-Cl | 4 | 4 |
| 1 | CONH$_2$ | -C₆H₄-C₆H₅ | 16 | 8 | 12 | SO$_2$NH$_2$ | -C₆H₄-C₆H₂Cl₃ | 2 | 1 |
| 2 | CONH$_2$ | -C₆H₄-C₆H₄-Cl | 4 | 2 | 13 | SO$_2$NH$_2$ | naphthyl | 16 | 8 |
| 3 | CONH$_2$ | -C₆H₄-C₆H₃Cl₂ | 8 | 2 | 14 | SO$_2$CH$_3$ | -C₆H₄-F | >64 | >64 |
| 4 | CONH$_2$ | -C₆H₄-C₆H₄-CH$_3$ | 8 | 8 | 15 | SO$_2$CH$_3$ | -C₆H₄-C₆H₄-CH$_3$ | >64 | >64 |
| 5 | CONH$_2$ | -C₆H₄-C₆H₄-CF$_3$ | >64 | >64 | 16 | NH$_2$ | -C₆H₄-C₆H₅ | 4 | 4 |
| 6 | CONH$_2$ | -C₆H₄-C₆H₃(CH$_3$)$_2$ | >64 | >64 | 17 | NH$_2$ | -C₆H₄-C₆H₂Cl₃ | >64 | 4 |
| 7 | CONH$_2$ | -C₆H₄-C₆H₄-C(CH$_3$)$_3$ | >64 | >64 | 18 | NH$_2$ | naphthyl | 8 | 8 |
| 8 | CONH$_2$ | -C₆H₄-C₆H₄-(CH$_2$)$_3$CH$_3$ | >64 | >64 | 19 | NH$_2$ | methyl-methoxy-naphthyl | 8 | 8 |
| 9 | CONH$_2$ | anthracenyl | 8 | 8 | 20 | NH$_2$ | -C₆H₄-C₆H₄-Br | 4 | 4 |
| 10 | CONH$_2$ | -C₆H₄-(CH$_2$)$_3$CH$_3$ | 16 | 8 | 21 | H | phenanthrenyl | >64 | >64 |

(*Fn, *F. novicida*; data were obtained after 24 h and 48 h for Fn and LVS, respectively)

Figure 2

ANTI-*FRANCISELLA* AGENTS

CROSS-REFERENCE TO RELATED APPLICATIONS

This application is a divisional application of, and claims priority to, U.S. patent application Ser. No. 12/428,035, filed Apr. 22, 2009, which is incorporated herein by reference in its entirety.

GOVERNMENT FUNDING

The present invention was made with government support under award No. 1-U54-AI-057153, awarded by the NIH/NIAID Regional Center of Excellence for Bio-defense and Emerging Infectious Diseases Research Program. The Government may have certain rights in this invention.

BACKGROUND

*Francisella tularensis* is a gram-negative, facultative, highly virulent bacterium, which causes the zoonotic disease tularemia. Infection can occur through several routes, but pneumonic tularemia is the most severe clinical form, with a mortality rate up to 60 percent in the absence of treatment. *F. tularensis* can invade a range of host cells, but its primary target in vivo is the macrophage. Sjostedt, A, Curr. Opin. Microbiol. 6, p. 66-71 (2003). After being phagocytosed by macrophages, this intracellular pathogen can block the fusion of *Francisella*-containing phagosomes with lysosomes and escape from the phagosome into the cytosol where it multiplies. Following proliferation within macrophages, *F. tularensis* induces host cell apoptosis or pyroptosis leading to the release of bacteria and subsequent infection of new cells.

Because of the ease with which aerosolized organisms could potentially be deliberately disseminated, inflicting substantial morbidity and mortality on large numbers of people, *F. tularensis* has been recognized as a potential biological warfare agent and, consequently, has been classified as a Category A bioterrorism agent by the U.S. Centers for Disease Control and Prevention. Unfortunately, the current live attenuated vaccine derived from a type B strain of *F. tularensis* has serious drawbacks and is of limited utility in the face of a bioterror threat. Oyston et al., Nat. Rev. Microbiol. 2, p. 967-78 (2004). Moreover, it is believed that antibiotic-resistant strains of *F. tularensis* were created in the early 1990s as biological weapons. Dennis et al., JAMA, 285, p. 2763-73 (2001). Consequently, the development of novel, antibacterial agents against *F. tularensis* has become an important priority.

SUMMARY OF THE INVENTION

The present invention provides a number of celecoxib derivatives that demonstrate antibacterial activity against *F. tularensis*. Accordingly, one aspect of the invention provides a method of treating or preventing infection by *Francisella tularensis* in a subject, comprising administering a therapeutically effective amount of a composition including a celecoxib derivative, or a pharmaceutically acceptable salt thereof, as further defined herein. In some embodiments, the *Francisella tularensis* infection is inhibited in macrophage cells without significant toxicity to the macrophage cells, and in some embodiments the *Francisella tularensis* is antibiotic resistant. In further embodiments, the subject is a human.

Another aspect of the invention provides compounds according to formula I

In this aspect of the invention, $R^1$ of Formula I is selected from the group consisting of hydrogen, amino, amido, methylsulfinyl, and ethylsulfinyl moieties, and $R^2$ is an aryl group. Group $R^2$ of formula I is optionally substituted at substitutable positions with one of more moieties independently selected from halo, lower alkyl, lower haloalkyl, lower hydroxyalkyl, hydroxyl, nitro, amino, carboxyl, and cyano. This aspect of the invention also includes pharmaceutically acceptable salts of the compounds of formula (I).

Another aspect of the invention provides pharmaceutical compositions including a compound of formula I:

In this aspect of the invention, $R^1$ is selected from the group consisting of hydrogen, amino, amido, methylsulfinyl, and ethylsulfinyl moieties, and $R^2$ is an aryl group. Group $R^2$ of Formula I is optionally substituted at substitutable positions with one of more moieties independently selected from halo, lower alkyl, lower haloalkyl, lower hydroxyalkyl, hydroxyl, nitro, amino, carboxyl, and cyano. The compound of formula I, or a pharmaceutically acceptable salt thereof, is an active ingredient in the pharmaceutical composition, and is provided in combination with a pharmaceutically acceptable liquid or solid carrier or carriers.

BRIEF DESCRIPTION OF THE FIGURES

FIG. 2 provides a table showing the structures and characteristics of celecoxib and compounds 1-21. The general structure of these molecules is shown at the top. Each test group was treated in triplicate and values shown are the results from one of three independent experiments.

DETAILED DESCRIPTION OF THE INVENTION

Figure 1:
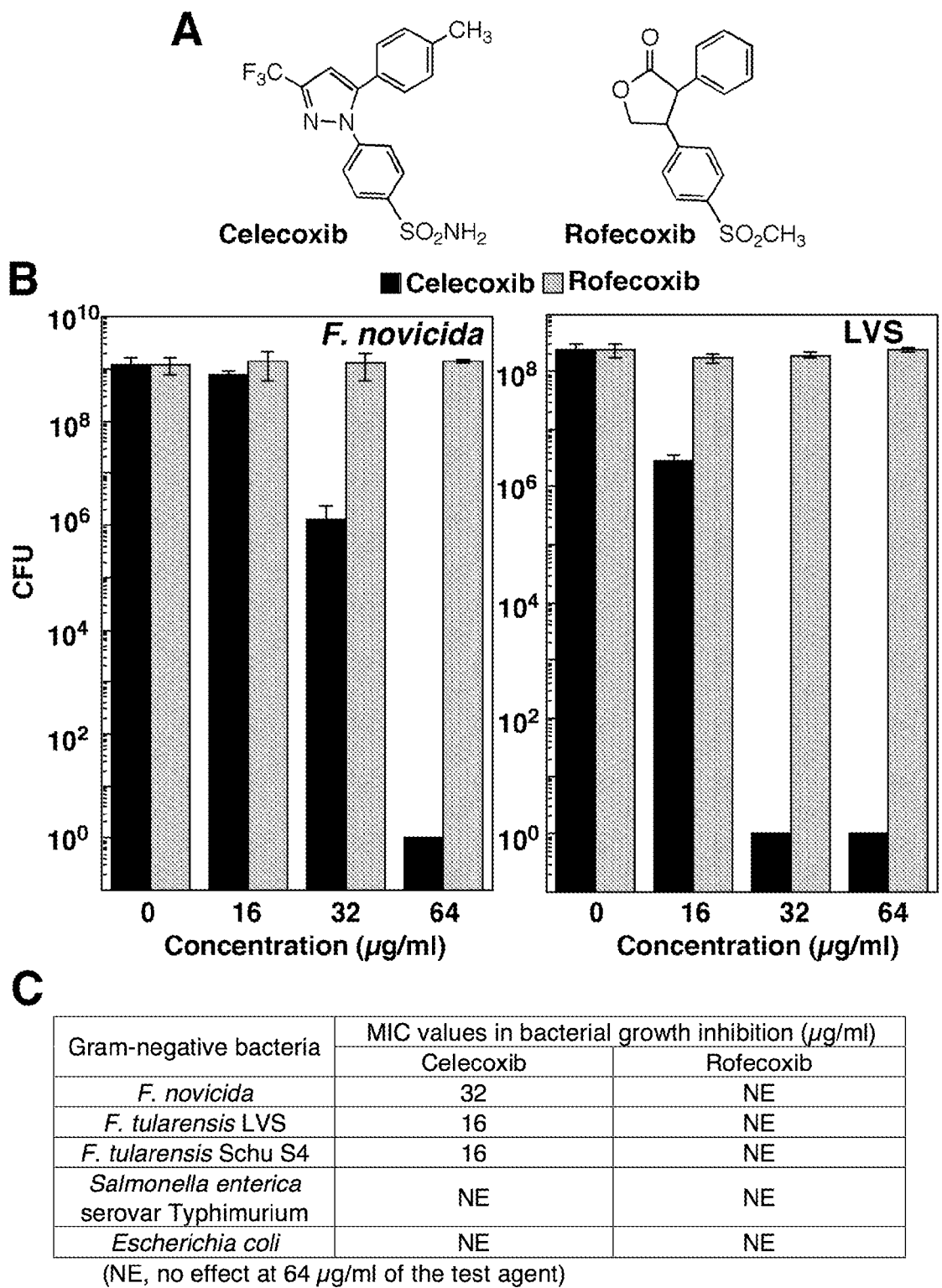
FIG. 1 shows the inhibition of *F. tularensis* growth by celecoxib in broth culture, with section (A) showing the structures of COX-2-specific inhibitors celecoxib (left) and rofecoxib (right), and section (B) providing a bar graph showing the results of a bacteria viability assay. *F. novicida* and LVS were cultured in modified TSB containing different doses of celecoxib or rofecoxib at 37° C. Viable *F. novicida* and LVS were measured as CFU after 24 or 48 h of incubation, respectively. Columns, mean; bars, ±SD (n=3). Section (C) provides a table showing the results of the minimum inhibitory concentration (MIC) assay. Each test group was treated in triplicate and values shown are the results from one of three independent experiments.

The inventors have demonstrated that the cyclooxygenase-2 (COX-2)-specific inhibitor celecoxib (4-[5-(4-methylphenyl)-3-(trifluoromethyl)pyrazol-1-yl]benzenesulfonamide) exhibits antibacterial activity against a virulent type A strain of *F. tularensis* (Schu S4), the live vaccine strain (LVS) of *F. tularensis* (type B strain) and *F. tularensis* subspecies *novicida* (an avirulent subspecies) directly in growth medium. This bacterial killing, however, was not noted with another COX-2 specific inhibitor, rofecoxib, despite its higher potency relative to celecoxib in COX-2 inhibition. Tacconelli et al., Curr. Med. Res. Opin. 18, p. 503-11 (2002). From a drug discovery perspective, the unique ability of celecoxib to inhibit the proliferation of *F. tularensis* can be pharmacologically exploited as a molecular platform to develop novel anti-*Francisella* agents.

DEFINITIONS

The terminology as set forth herein is for description of the embodiments only and should not be construed as limiting of the invention as a whole. Unless otherwise specified, "a," "an," "the," and "at least one" are used interchangeably. Furthermore, as used in the description of the invention and the appended claims, the singular forms "a", "an", and "the" are inclusive of their plural forms, unless contraindicated by the context surrounding such.

The terms "comprising" and variations thereof do not have a limiting meaning where these terms appear in the description and claims.

As used herein, the term "organic group" is used for the purpose of this invention to mean a hydrocarbon group that is classified as an aliphatic group, cyclic group, or combination of aliphatic and cyclic groups (e.g., alkaryl and aralkyl groups). In the context of the present invention, suitable organic groups for celecoxib derivatives are those that do not interfere with the celecoxib derivative's anti-francisella activity. In the context of the present invention, the term "aliphatic group" means a saturated or unsaturated linear or branched hydrocarbon group. This term is used to encompass alkyl, alkenyl, and alkynyl groups, for example.

As used herein, the terms "alkyl", "alkenyl", and the prefix "alk-" are inclusive of straight chain groups and branched chain groups and cyclic groups, e.g., cycloalkyl and cycloalkenyl. Unless otherwise specified, these groups contain from 1 to 20 carbon atoms, with alkenyl groups containing from 2 to 20 carbon atoms. In some embodiments, these groups have a total of at most 10 carbon atoms, at most 8 carbon atoms, at most 6 carbon atoms, or at most 4 carbon atoms. Lower alkyl groups are those including at most 6 carbon atoms. Examples of alkyl groups include haloalkyl groups and hydroxyalkyl groups. Cyclic groups can be monocyclic or polycyclic and preferably have from 3 to 10 ring carbon atoms.

Unless otherwise specified, "alkylene" and "alkenylene" are the divalent forms of the "alkyl" and "alkenyl" groups defined above. The terms, "alkylenyl" and "alkenylenyl" are used when "alkylene" and "alkenylene", respectively, are substituted. For example, an arylalkylenyl group comprises an alkylene moiety to which an aryl group is attached.

The term "haloalkyl" is inclusive of groups that are substituted by one or more halogen atoms, including perfluorinated groups. This is also true of other groups that include the prefix "halo-". Examples of suitable haloalkyl groups are chloromethyl, trifluoromethyl, and the like. A halo moiety can be chlorine, bromine, fluorine, or iodine.

The term "aryl" as used herein includes carbocyclic aromatic rings or ring systems. Examples of aryl groups include phenyl, naphthyl, biphenyl, anthracenyl, phenanthracenyl, fluorenyl and indenyl. Aryl groups may be substituted or unsubstituted.

Unless otherwise indicated, the term "heteroatom" refers to the atoms O, S, or N.

The term "heteroaryl" includes aromatic rings or ring systems that contain at least one ring heteroatom (e.g., O, S, N). In some embodiments, the term "heteroaryl" includes a ring or ring system that contains 2 to 12 carbon atoms, 1 to 3 rings, 1 to 4 heteroatoms, and O, S, and/or N as the heteroatoms. Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

The terms "arylene" and "heteroarylene" are the divalent forms of the "aryl" and "heteroaryl" groups defined above. The terms "arylenyl" and "heteroarylenyl" are used when "arylene" and "heteroarylene", respectively, are substituted. For example, an alkylarylenyl group comprises an arylene moiety to which an alkyl group is attached.

When a group is present more than once in any formula or scheme described herein, each group (or substituent) is independently selected, whether explicitly stated or not. For example, for the formula —C(O)—NR$_2$ each R group is independently selected.

As a means of simplifying the discussion and the recitation of certain terminology used throughout this application, the terms "group" and "moiety" are used to differentiate between chemical species that allow for substitution or that may be substituted and those that do not so allow for substitution or may not be so substituted. Thus, when the term "group" is used to describe a chemical substituent, the described chemical material includes the unsubstituted group and that group with nonperoxidic O, N, S, Si, or F atoms, for example, in the chain as well as carbonyl groups or other conventional substituents. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, tert-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, sulfoalkyls, etc. On the other hand, the phrase "alkyl moiety" is limited to the inclusion of only pure open chain saturated hydrocarbon alkyl substituents, such as methyl, ethyl, propyl, tert-butyl, and the like.

"Treat", "treating", and "treatment", etc., as used herein, refer to any action providing a benefit to a patient at risk for or afflicted with a disease, including improvement in the condition through lessening or suppression of at least one symptom, delay in progression of the disease, prevention or delay in the onset of the disease, etc.

Macrophage cells, as used herein, refers to immune cells of the innate immune system, and include macrophages, macrophage-like cells, and macrophage precursors such as monocytes. Macrophage-like cells include tingible body macrophages, dendritic cells, foam cells, and multinucleated giant cells.

Antibiotics, as defined herein, are bactericidal or bacteriostatic compounds already known in the art. Examples of known antibiotics include agents that target the bacterial cell wall, such as penicillins, cephalosporins, agents that target the cell membrane such as polymixins, agents that interfere with essential bacterial enzymes, such as quinolones and sulfonamides, and agents that that target protein synthesis such as the aminoglycosides, macrolides and tetracyclines. Additional known antibiotics include cyclic lipopeptides, glycylcyclines, and oxazolidinones.

"Pharmaceutically acceptable" as used herein means that the compound or composition is suitable for administration to a subject to achieve the treatments described herein, without unduly deleterious side effects in light of the severity of the disease and necessity of the treatment.

"Inhibit" as used herein refers to the partial or complete elimination of a potential effect, while inhibitors are compounds that have the ability to inhibit.

Celecoxib Derivatives

Celecoxib derivatives, as defined herein, include the compounds of formula I:

(I)

Formula 1 provides 3-trifluoromethyl pyrazolyl 1-phenyl core to which is attached an organic group $R^1$ at the 4' position of the phenyl group and an organic group $R^2$ at the 5' position of the pyrazolyl group. In celecoxib derivatives, which as defined herein includes celecoxib itself, the organic group $R^1$ is selected from the group consisting of hydrogen, amino, amido, methylsulfinyl, and ethylsulfinyl moieties, and the organic group $R^2$ is an aryl group. The aryl group $R^2$ is optionally substituted at substitutable positions with one or more moieties independently selected from halo, lower alkyl, lower haloalkyl, lower hydroxyalkyl, hydroxyl, nitro, amino, carboxyl, and cyano.

In embodiments of the invention, the $R^2$ aryl group is selected from the group consisting of phenyl, naphthyl, biphenyl, anthracenyl, and phenanthracenyl aryl groups. In further embodiments, the optional substituting moieties for $R^2$ are independently selected from bromo, chloro, fluoro, methoxy, trifluoromethyl, methyl, ethyl, propyl, and butyl.

Examples of celecoxib derivatives that can be used for the treatment of *Francisella tularensis* infection include celecoxib, as well as the non-celexoxib derivatives 4-(5-biphenyl-4-yl-3-trifluoromethyl-pyrazol-1-yl)-benzamide (Compound 1); 4-[5-(4'-chloro-biphenyl-4-yl)-3-trifluoromethyl-pyrazol-1-yl]-benzamide (Compound 2); 4-[5-(3',5'-dichloro-biphenyl-4-yl)-3-trifluoromethyl-pyrazol-1-yl]-benzamide (Compound 3); 4-[5-(4'-methyl-biphenyl-4-yl)-3-trifluoromethyl-pyrazol-1-yl]-benzamide (Compound 4); 4-[3-trifluoromethyl-5-(4'-trifluoromethyl-biphenyl-4-yl)-pyrazol-1-yl]-benzamide (Compound 5);

4-[5-(3',5'-dimethyl-biphenyl-4-yl)-3-trifluoromethyl-pyrazol-1-yl]-benzamide (Compound 6); 4-[5-(4'-tert-butyl-biphenyl-4-yl)-3-trifluoromethyl-pyrazol-1-yl]-benzamide (Compound 7); 4-[5-(4'-butyl-biphenyl-4-yl)-3-trifluoromethyl-pyrazol-1-yl]-benzamide (Compound 8); 4-(5-anthracen-9-yl-3-trifluoromethyl-pyrazol-1-yl)-benzamide (Compound 9); and 4-[5-(4-butyl-phenyl)-3-trifluoromethyl-pyrazol-1-yl]-benzamide (Compound 10).

Celecoxib derivatives further include 4-[5-(4'-chloro-biphenyl-4-yl)-3-trifluoromethyl-pyrazol-1-yl]-benzenesulfonamide (Compound 11); 4-[5-(3',4',5'-trichloro-biphenyl-4-yl)-3-trifluoromethyl-pyrazol-1-yl]-benzenesulfonamide (Compound 12); 4-(5-naphthalen-1-yl-3-trifluoromethyl-pyrazol-1-yl)-benzenesulfonamide (Compound 13); 5-(4-fluoro-phenyl)-1-(4-ethanesulfonyl-phenyl)-3-trifluoromethyl-1H-pyrazole (Compound 14); 1-(4-methanesulfonyl-phenyl)-5-(4'-methyl-biphenyl-4-yl)-3-trifluoromethyl-1H-pyrazole (Compound 15); 4-(5-biphenyl-4-yl-3-trifluoromethyl-pyrazol-1-yl)-phenylamine (Compound 16); 4-[5-(3',4',5'-trichloro-biphenyl-4-yl)-3-trifluoromethyl-pyrazol-1-yl]-phenylamine (Compound 17); 4-(5-naphthalen-1-yl-3-trifluoromethyl-pyrazol-1-yl)-phenylamine (Compound 18); 4-[5-(6-methoxy-naphthalen-2-yl)-3-trifluoromethyl-pyrazol-1-yl]-phenylamine (Compound 19); 4-[5-(4'-bromo-biphenyl-4-yl)-3-trifluoromethyl-pyrazolyl]-phenylamine (Compound 20); and 5-phenanthren-3-yl-1-phenyl-3-trifluoromethyl-1H-pyrazole (Compound 21).

In additional embodiments of the invention, celecoxib derivatives that exhibit higher activity (e.g., they exhibit lower minimum inhibitory concentration against *Francisella tularensis*) may be preferred. For example, some embodiments include the compounds celecoxib, 4-[5-(4'-chloro-biphenyl-4-yl)-3-trifluoromethyl-pyrazol-1-yl]-benzamide (Compound 2); 4-[5-(4'-chloro-biphenyl-4-yl)-3-trifluoromethyl-pyrazol-1-yl]-benzenesulfonamide (Compound 11); 4-[5-(3',4',5'-trichloro-biphenyl-4-yl)-3-trifluoromethyl-pyrazol-1-yl]-benzenesulfonamide (Compound 12); 4-(5-biphenyl-4-yl-3-trifluoromethyl-pyrazol-1-yl)-phenylamine (Compound 16); and 4-[5-(4'-bromo-biphenyl-4-yl)-3-trifluoromethyl-pyrazolyl]-phenylamine (Compound 20). In an additional embodiment, the compound is 4-[5-(4'-bromo-biphenyl-4-yl)-3-trifluoromethyl-pyrazolyl]-phenylamine (Compound 20) is preferred. Additional embodiments of the use of celecoxib derivatives for treating infection with *Francisella tularensis* also include the pharmaceutically acceptable salts of these compounds.

While the compound celecoxib is already known for use as an antiarthritic agent, and a number of substituted pyrazolyl benzenesulfonamides have been prepared for treating inflammation, as described in U.S. Pat. No. 5,466,823 issued to Talley et al., many of the celecoxib derivatives described herein have not previously been prepared. Accordingly, another aspect of the invention claims the celecoxib derivatives that do not include benzenesulfonamide, as encompassed by Formula I:

$$\underset{F}{\overset{F}{\underset{F}{\bigvee}}}\overset{R^2}{\underset{N-N}{\bigvee}}\overset{(I)}{\underset{R^1}{\bigvee}}$$

wherein R¹ is selected from the group consisting of hydrogen, amino, amido, methylsulfinyl, and ethylsulfinyl moieties, and R² is an aryl group, and wherein R² is optionally substituted at substitutable positions with one of more moieties independently selected from halo, lower alkyl, lower haloalkyl, lower hydroxyalkyl, hydroxyl, nitro, amino, carboxyl, and cyano.

Further embodiments are directed to these compounds wherein the R² aryl group is selected from the group consisting of phenyl, naphthyl, biphenyl, anthracenyl, and phenanthracenyl aryl groups, and further wherein the optional substituting moieties for R² are independently selected from bromo, chloro, fluoro, methoxy, trifluoromethyl, methyl, ethyl, propyl, and butyl.

Additional celecoxib compounds that do not include the benzenesulfaonamide group are 4-(5-biphenyl-4-yl-3-trifluoromethyl-pyrazol-1-yl)-benzamide (Compound 1); 4-[5-(4'-chloro-biphenyl-4-yl)-3-trifluoromethyl-pyrazol-1-yl]-benzamide (Compound 2); 4-[5-(3',5'-dichloro-biphenyl-4-yl)-3-trifluoromethyl-pyrazol-1-yl]-benzamide (Compound 3); 4-[5-(4'-methyl-biphenyl-4-yl)-3-trifluoromethyl-pyrazol-1-yl]-benzamide (Compound 4); 4-[3-trifluoromethyl-5-(4'-trifluoromethyl-biphenyl-4-yl)-pyrazol-1-yl]-benzamide (Compound 5); 4-[5-(3',5'-dimethyl-biphenyl-4-yl)-3-trifluoromethyl-pyrazol-1-yl]-benzamide (Compound 6); 4-[5-(4'-tert-butyl-biphenyl-4-yl)-3-trifluoromethyl-pyrazol-1-yl]-benzamide (Compound 7); 4-[5-(4'-butyl-biphenyl-4-yl)-3-trifluoromethyl-pyrazol-1-yl]-benzamide (Compound 8); 4-(5-anthracen-9-yl-3-trifluoromethyl-pyrazol-1-yl)-benzamide (Compound 9); and 4-[5-(4-butyl-phenyl)-3-trifluoromethyl-pyrazol-1-yl]-benzamide (Compound 10); 5-(4-fluoro-phenyl)-1-(4-ethanesulfonyl-phenyl)-3-trifluoromethyl-1H-pyrazole (Compound 14); 1-(4-methanesulfonyl-phenyl)-5-(4'-methyl-biphenyl-4-yl)-3-trifluoromethyl-1H-pyrazole (Compound 15); 4-(5-biphenyl-4-yl-3-trifluoromethyl-pyrazol-1-yl)-phenylamine (Compound 16); 4-[5-(3',4',5'-trichloro-biphenyl-4-yl)-3-trifluoromethyl-pyrazol-1-yl]-phenylamine (Compound 17); 4-(5-naphthalen-1-yl-3-trifluoromethyl-pyrazol-1-yl)-phenylamine (Compound 18); 4-[5-(6-methoxy-naphthalen-2-yl)-3-trifluoromethyl-pyrazol-1-yl]-phenylamine (Compound 19); 4-[5-(4'-bromo-biphenyl-4-yl)-3-trifluoromethyl-pyrazolyl]-phenylamine (Compound 20); and 5-phenanthren-3-yl-1-phenyl-3-trifluoromethyl-1H-pyrazole (Compound 21), as well as the pharmaceutically acceptable salts of these compounds.

Additional embodiments of the invention are directed to celecoxib derivatives that do not include benzenesulfonamide and that exhibit relatively high activity. For example, one embodiment includes the compounds 4-[5-(4'-chloro-biphenyl-4-yl)-3-trifluoromethyl-pyrazol-1-yl]-benzamide (Compound 2);

4-(5-biphenyl-4-yl 3-trifluoromethyl-pyrazol-1-yl)-phenylamine (Compound 16); and 4-[5-(4'-bromo-biphenyl-4-yl)-3-trifluoromethyl-pyrazolyl]-phenylamine (Compound 20); while a further embodiment is directed specifically to 4-[5-(4'-bromo-biphenyl-4-yl)-3-trifluoromethyl-pyrazolyl]-phenylamine (Compound 20).

Additional embodiments include the pharmaceutically acceptable salts of these compounds.

Treatment of *Francesella tularensis* Using Celecoxib Derivatives

The present invention provides methods for treating or preventing infection by *Francisella tularensis* in a subject using celecoxib derivatives. *Francisella tularensis* is a pathogenic species of gram-negative bacteria that is the causative agent of tularemia; also known as rabbit fever. *Francisella tularensis* includes the subspecies *tularensis* (type A), *palearctica* (type B), *novicida*, and *mediasiatica*.

Treatment, as used herein, encompasses both prophylactic and therapeutic treatment. Celecoxib derivatives of the invention can, for example, be administered prophylactically to a mammal prior to exposure to infection by *Francisella tularensis*. Prophylactic administration, also referred to as prevention, is effective to decrease the likelihood of the subsequent infection in the mammal, or decrease the severity of *Francisella* infection that subsequently occurs. Alternatively, celecoxib derivatives of the invention can, for example, be administered therapeutically to a subject that is already infected by *Francisella tularensis*. In one embodiment of therapeutic administration, administration of the celecoxib derivatives are effective to eliminate the infection; in another embodiment, administration of the celecoxib derivatives is effective to decrease the severity of the infection. The subject is preferably a mammal, such as a domesticated farm animal (e.g., cow, horse, pig) or pet (e.g., dog, cat). More preferably, the subject is a human.

In some embodiments, the *Francisella tularensis* infection is inhibited in macrophage cells, which are the primary in vivo target for *F. tularensis*. As shown in the examples provided herein, celecoxib derivatives are able to effectively inhibit *F. tularensis* in macrophages. In additional embodiments, the celecoxib derivatives are able to inhibit *F. tularensis* in macrophages without significant toxicity to other cells, and macrophage cells in particular.

The celecoxib derivatives can also be administered to subjects to treat or prevent infection by antibiotic resistant strains of *Francisella tularensis*. Celecoxib has been shown inhibitory activity against a number of mammalian enzymes, including phosphoinositide-dependent kinase-1, carbonic anhydrase, sarcoplasmic/ER calcium ATPase, and COX-1, as further described herein. Antibiotic resistance can develop through various mechanisms, such as drug inactivation or modification, alteration of target site, or alteration of a metabolic pathway that the antibiotic affects. Accordingly, providing treatment with compounds having a different structure and different target sites, as exhibited by the celecoxib derivatives described herein, can circumvent existing antibiotic resistance in many situations.

Administration and Formulation of Celecoxib Derivatives

The present invention also provides pharmaceutical compositions that include celecoxib derivatives according to formula I as an active ingredient, and a pharmaceutically acceptable liquid or solid carrier or carriers, in combination with the active ingredient. Any of the compounds described above as being suitable for the treatment of *Francisella tularensis* can be included in pharmaceutical compositions of the invention.

The celecoxib derivatives can be administered as pharmaceutically acceptable salts. Pharmaceutically acceptable salt refers to the relatively non-toxic, inorganic and organic acid addition salts of the celecoxib derivatives. These salts can be prepared in situ during the final isolation and purification of the celecoxib derivative, or by separately reacting a purified celecoxib derivative with a suitable counterion, depending on the nature of the celecoxib derivative, and isolating the salt thus formed. Representative counterions include the chloride, bromide, nitrate, ammonium, sulfate, tosylate, phosphate, tartrate, ethylenediamine, and maleate salts, and the like. See for example Haynes et al., J. Pharm. Sci., 94, p. 2111-2120 (2005).

The pharmaceutical compositions includes one or more celecoxib derivatives together with one or more of a variety of physiological acceptable carriers for delivery to a patient, including a variety of diluents or excipients known to those of ordinary skill in the art. For example, for parenteral administration, isotonic saline is preferred. For topical administration, a cream, including a carrier such as dimethylsulfoxide (DMSO), or other agents typically found in topical creams that do not block or inhibit activity of the peptide, can be used. Other suitable carriers include, but are not limited to, alcohol, phosphate buffered saline, and other balanced salt solutions.

The formulations may be conveniently presented in unit dosage form and may be prepared by any of the methods well known in the art of pharmacy. Preferably, such methods include the step of bringing the active agent into association with a carrier that constitutes one or more accessory ingredients. In general, the formulations are prepared by uniformly and intimately bringing the active agent into association with a liquid carrier, a finely divided solid carrier, or both, and then, if necessary, shaping the product into the desired formulations. The methods of the invention include administering to a subject, preferably a mammal, and more preferably a human, the composition of the invention in an amount effective to produce the desired effect. The celecoxib derivatives can be administered as a single dose or in multiple doses. Useful dosages of the active agents can be determined by comparing their in vitro activity and the in vivo activity in animal models. Methods for extrapolation of effective dosages in mice, and other animals, to humans are known in the art; for example, see U.S. Pat. No. 4,938,949.

The agents of the present invention are preferably formulated in pharmaceutical compositions and then, in accordance with the methods of the invention, administered to a subject, such as a human patient, in a variety of forms adapted to the chosen route of administration. The formulations include, but are not limited to, those suitable for oral, rectal, vaginal, topical, nasal, ophthalmic, or parental (including subcutaneous, intramuscular, intraperitoneal, intratumoral, and intravenous) administration.

Formulations of the present invention suitable for oral administration may be presented as discrete units such as tablets, troches, capsules, lozenges, wafers, or cachets, each containing a predetermined amount of the active agent as a powder or granules, as liposomes containing the celecoxib derivatives, or as a solution or suspension in an aqueous liquor or non-aqueous liquid such as a syrup, an elixir, an emulsion, or a draught. Such compositions and preparations typically contain at least about 0.1 wt-% of the active agent. The amount of celecoxib derivatives (i.e., active agent) is such that the dosage level will be effective to produce the desired result in the subject.

Nasal spray formulations include purified aqueous solutions of the active agent with preservative agents and isotonic agents. Such formulations are preferably adjusted to a pH and isotonic state compatible with the nasal mucous membranes.

Formulations for rectal or vaginal administration may be presented as a suppository with a suitable carrier such as cocoa butter, or hydrogenated fats or hydrogenated fatty carboxylic acids. Ophthalmic formulations are prepared by a similar method to the nasal spray, except that the pH and isotonic factors are preferably adjusted to match that of the eye. Topical formulations include the active agent dissolved or suspended in one or more media such as mineral oil, petroleum, polyhydroxy alcohols, or other bases used for topical pharmaceutical formulations.

The tablets, troches, pills, capsules, and the like may also contain one or more of the following: a binder such as gum tragacanth, acacia, corn starch or gelatin; an excipient such as dicalcium phosphate; a disintegrating agent such as corn starch, potato starch, alginic acid, and the like; a lubricant such as magnesium stearate; a sweetening agent such as sucrose, fructose, lactose, or aspartame; and a natural or artificial flavoring agent. When the unit dosage form is a capsule, it may further contain a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, sugar, and the like. A syrup or elixir may contain one or more of a sweetening agent, a preservative such as methyl- or propylparaben, an agent to retard crystallization of the sugar, an agent to increase the solubility of any other ingredient, such as a polyhydric alcohol, for example glycerol or sorbitol, a dye, and flavoring agent. The material used in preparing any unit dosage form is substantially nontoxic in the amounts employed. The active agent may be incorporated into sustained-release preparations and devices.

Preparation of the Compounds

Compounds of the invention may be synthesized by synthetic routes that include processes similar to those well known in the chemical arts, particularly in light of the description contained herein. The starting materials are generally available from commercial sources such as Aldrich Chemicals (Milwaukee, Wis., USA) or are readily prepared using methods well known to those skilled in the art (e.g., prepared by methods generally described in Louis F. Fieser and Mary Fieser, *Reagents for Organic Synthesis*, v. 1-19, Wiley, New York, (1967-1999 ed.); Alan R. Katritsky, Otto Meth-Cohn, Charles W. Rees, *Comprehensive Organic Functional Group Transformations*, v 1-6, Pergamon Press, Oxford, England, (1995); Barry M. Trost and Ian Fleming, *Comprehensive Organic Synthesis*, v. 1-8, Pergamon Press, Oxford, England, (1991); or *Beilsteins Handbuch der organischen Chemie*, 4, Aufl. Ed. Springer-Verlag, Berlin, Germany, including supplements (also available via the Beilstein online database)).

Those skilled in the art will appreciate that other synthetic routes may be used to synthesize the compounds of the invention. Although specific starting materials and reagents are depicted in the reaction schemes and discussed below, other starting materials and reagents can be easily substituted to provide a variety of derivatives and/or reaction conditions. In addition, many of the compounds prepared by the methods described below can be further modified in light of this disclosure using conventional methods well known to those skilled in the art.

The present invention is illustrated by the following examples. It is to be understood that the particular examples, materials, amounts, and procedures are to be interpreted broadly in accordance with the scope and spirit of the invention as set forth herein.

EXAMPLES

Example 1

General Procedures for
1,1,1-trifluoro-4-aryl-but-3-en-2-one Intermediates

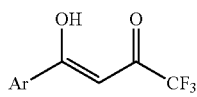

To a suspension of sodium hydride (NaH; 0.13 g, 5.4 mmol) in 5 ml of anhydrous tetrahydrofuran (THF) was added ethyl trifluoroacetate ($CF_3COOEt$; 0.64 g, 4.5 mmol) under argon. After stirring at 25° C. for 10 min, 4-substituted phenyl (4.5 mmol) in 5 ml of THF was added dropwise to the solution. The mixture became clear and orange hued within 30 min, and after stirring for an additional 2 h, was concentrated under vacuum. The residue was suspended in water, and extracted with ethyl acetate (15 ml) twice. The organic phase was separated, dried over sodium sulfate, and concentrated to dryness under vacuum to give the product (yellow solid; 1.29 g, 90% yield). The product was used directly without purification.

1,1,1-Trifluoro-4-hydroxy-4-(4'-methyl-biphenyl-4-yl)-but-3-en-2-one;

4-(4'-Chloro-biphenyl-4-yl)-1,1,1-trifluoro-4-hydroxy-but-3-en-2-one;

4-(3',5'-Dichloro-biphenyl-4-yl)-1,1,1-trifluoro-4-hydroxy-but-3-en-2-one;

4-(4'-Methyl-biphenyl-4-yl)-1,1,1-trifluoro-4-hydroxy-but-3-en-2-one;

4-(4'-Trifluoromethyl-biphenyl-4-yl)-1,1,1-trifluoro-4-hydroxy-but-3-en-2-one;

4-(3',5'-Dimethyl-biphenyl-4-yl)-1,1,1-trifluoro-4-hydroxy-but-3-en-2-one;

4-(4'-t-Butyl-biphenyl-4-yl)-1,1,1-trifluoro-4-hydroxy-but-3-en-2-one;

4-(4'-n-Butyl-biphenyl-4-yl)-1,1,1-trifluoro-4-hydroxy-but-3-en-2-one;

4-Anthracen-9-yl-1,1,1-trifluoro-4-hydroxy-but-3-en-2-one;

4-(4-Butyl-phenyl)-1,1,1-trifluoro-4-hydroxy-but-3-en-2-one;

4-(2',4',5'-Trichloro-biphenyl-4-yl)-1,1,1-trifluoro-4-hydroxy-but-3-en-2-one;

1,1,1-Trifluoro-4-hydroxy-4-naphthalen-1-yl-but-3-en-2-one;

4-(4-Fluoro-phenyl)-1,1,1-trifluoro-4-hydroxy-but-3-en-2-one;

1,1,1-Trifluoro-4-hydroxy-4-(6-methoxy-naphthalen-2-yl)-but-3-en-2-one;

4-(4'-Bromo-biphenyl-4-yl)-1,1,1-trifluoro-4-hydroxy-but-3-en-2-one;

1,1,1-Trifluoro-4-hydroxy-4-phenanthren-3-yl-but-3-en-2-one.

Example 2

General Procedures for 4-Carboxamide Compounds

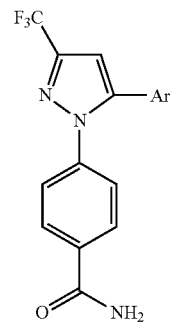

(4-Carbamoylphenyl)-hydrazine hydrochloride (0.92 g, 4.9 mmol) was added to a stirred solution of precursors (I to X) (4.1 mmol) in 40 ml of ethanol at 25° C. to prepare compounds 1-10, below. The mixture was refluxed for 12 h, cooled to room temperature and concentrated to dryness under vacuum. The residue was dissolved in ethyl acetate, and washed with water. The organic layer was dried over sodium sulfate, and concentrated under vacuum. The crude product was purified by silica gel flash chromatography (ethyl acetate-hexane, 1:1), yielding 1 to 10 respectively in good yield.

Compound 1: 4-(5-Biphenyl-4-yl-3-trifluoromethyl-pyrazol-1-yl)-benzamide;

Compound 2: 4-[5-(4'-Chloro-biphenyl-4-yl)-3-trifluoromethyl-pyrazol-1-yl]-benzamide;

Compound 3: 4-[5-(3',5'-Dichloro-biphenyl-4-yl)-3-trifluoromethyl-pyrazol-1-yl]-benzamide;

Compound 4: 4-[5-(4'-Methyl-biphenyl-4-yl)-3-trifluoromethyl-pyrazol-1-yl]-benzamide;

Compound 5: 4-[3-Trifluoromethyl-5-(4'-trifluoromethyl-biphenyl-4-yl)-pyrazol-1-yl]-benzamide;

Compound 6: 4-[5-(3,5'-Dimethyl-biphenyl-4-yl)-3-trifluoromethyl-pyrazol-1-yl]-benzamide;

Compound 7: 4-[5-(4'-t-Butyl-biphenyl-4-yl)-3-trifluoromethyl-pyrazol-1-yl]-benzamide;

Compound 8: 4-[5-(4'-n-Butyl-biphenyl-4-yl)-3-trifluoromethyl-pyrazol-1-yl]-benzamide;

Compound 9: 4-(5-Anthracen-9-yl-3-trifluoromethyl-pyrazol-1-yl)-benzamide;

Compound 10: 4-[5-(4-Butyl-phenyl)-3-trifluoromethyl-pyrazol-1-yl]-benzamide.

Example 3

General Procedures for 4-Sulfonamide Compounds (11-13)

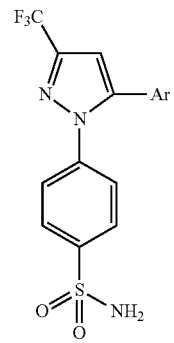

4-Hydrazinobenzene-1-sulfonamide hydrochloride (1.1 g, 4.9 mmol) was added to a stirred solution of precursors (II, XI and XII) (4.1 mmol) in 40 ml of ethanol. The mixture was refluxed for 12 h, cooled to room temperature, and concentrated to dryness under vacuum. The residue was dissolved in ethyl acetate, and washed with water. The organic layer was dried over sodium sulfate, and concentrated under vacuum. The crude product was purified by silica gel flash chromatography to yield 11, 12, 13 respectively.
Compound 11: 4-[5-(4'-Chloro-biphenyl-4-yl)-3-trifluoromethyl-pyrazol-1-yl]-benzenesulfonamide;
Compound 12: 4-[5-(2',4',5'-Trichloro-biphenyl-4-yl)-3-trifluoromethyl-pyrazol-1-yl]-benzenesulfonamide;
Compound 13: 4-(5-Naphthalen-1-yl-3-trifluoromethyl-pyrazol-1-yl)-benzenesulfonamide.

Example 4

General Procedures for 4-Methanesulfonyl Compounds

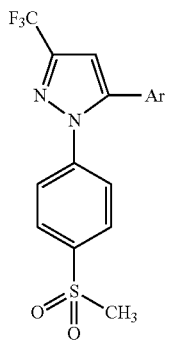

(4-Methanesulfonyl-phenyl)-hydrazine hydrochloride (4.9 mmol) was added to a stirred solution of precursors (XIII, IV) (4.1 mmol) in 40 ml of ethanol. The mixture was refluxed for 12 h, cooled to room temperature, and concentrated to dryness under vacuum. The residue was dissolved in ethyl acetate, and washed with water. The organic layer was dried over sodium sulfate, and concentrated under vacuum. The crude product was purified by silica gel flash chromatography to yield 14 and 15 respectively.

Compound 14: 5-(4-Fluoro-phenyl)-1-(4-methanesulfonyl-phenyl)-3-trifluoromethyl-1H-pyrazole;

Compound 15: 1-(4-Methanesulfonyl-phenyl)-5-(4'-methyl-biphenyl-4-yl)-3-trifluoromethyl-1H-pyrazole.

Example 5

General Procedures for 4-Amine Compounds

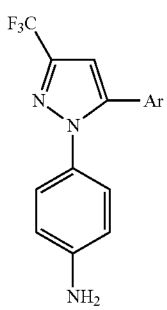

To a solution of precursors I, XI, XII, XIV, and XV (4.1 mmol) in 40 ml of ethanol was added 4-nitrophenylhydrazine hydrochloride (4.9 mmol) respectively under stirring, refluxed for 1 h, cooled to room temperature, and concentrated to dryness under vacuum. The residue was dissolved in ethyl acetate, and washed with water. The organic phase was dried over magnesium sulfate, and concentrated to dryness under vacuum. The crude product was purified by silica gel column chromatography to afford nitro compounds XVII, XVIII, XIX, XX, and XXI respectively in fair to good yield.

XVII. 5-Biphenyl-4-yl-1-(4-nitro-phenyl)-3-trifluoromethyl-1H-pyrazole

XVIII. 5-(2',4',5'-Trichloro-biphenyl-4-yl)-1-(4-nitro-phenyl)-3-trifluoromethyl-1H-pyrazole XIX. 5-Naphthalen-1-yl-1-(4-nitro-phenyl)-3-trifluoromethyl-1H-pyrazole XX. 5-(6-methoxy-naphthalen-2-yl)-1-(4-nitro-phenyl)-3-trifluoromethyl-1H-pyrazole XXI. 5-(4'-Bromo-biphenyl-4-yl)-1-(4-nitro-phenyl)-3-trifluoromethyl-1H-pyrazole To a solution of nitro compounds XVII, XVIII, XIX, XX, and XXI (2 mmol) in 20 ml ethanol was added platinum oxide (27 mg, 0.12 mmol) respectively, stirred under $H_2$ at 55 psi for 12 h, filtered to remove the catalyst, and concentrated to dryness under vacuum. The crude product was purified by silica gel column chromatography to yield compounds 16, 17, 18, 19, and 20 respectively in good yield.

Compound 16: 4-(5-Biphenyl-4-yl-3-trifluoromethyl-pyrazol-1-yl)-phenylamine;

Compound 17: 4-[5-(2',4',5'-Trichloro-biphenyl-4-yl)-3-trifluoromethyl-pyrazol-1-yl]-phenylamine;

Compound 18: 4-(5-Naphthalen-1-yl-3-trifluoromethyl-pyrazol-1-yl)-phenylamine;

Compound 19: 4-[5-(6-methoxy-naphthalen-2-yl)-3-trifluoromethyl-pyrazol-1-yl)-phenylamine;

Compound 20: 4-[5-(4'-Bromo-biphenyl-4-yl)-3-trifluoromethyl-pyrazol-1-yl]-phenylamine.

Example 6

1-Phenyl-5-phenanthrenyl-3-(trifluoromethyl)-1H-pyrazole (21)

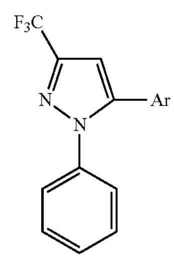

To a solution of XVI (4.1 mmol) in 40 ml of ethanol was added phenylhydrazine hydrochloride (4.9 mmol) under stirring, refluxed for 1 h, cooled to room temperature, and concentrated to dryness under vacuum. The residue was dissolved in ethyl acetate, and washed with water. The organic phase was dried over magnesium sulfate, and concentrated to dryness under vacuum. The crude product was purified by silica gel column chromatography to afford compound 21, (5-phenanthren-3-yl-1-phenyl-3-trifluoromethyl-1H-pyrazole) (0.88 g, 50% yield).

Example 7

Antibacterial Effect of Celecoxib and Celecoxib Derivatives Against *Francisella tularensis*

Materials and Methods

Bacteria

*F. novicida* strain U112, the live vaccine strain (LVS, type B), and *F. tularensis* strain Schu S4 (type A) were used throughout this study. Experiments involving Schu S4 were conducted in a CDC select agent-approved BSL3 laboratory at Ohio State University. Bacteria were grown at 37° C. on chocolate II agar (Becton, Dickinson and Company, Franklin Lakes, N.J.) or in tryptic soy broth (Becton, Dickinson and Company) supplemented with 0.025% (w/v) iron (III) pyrophosphate (Sigma-Aldrich, St. Louis, Mo.) and 0.1% (w/v) cysteine hydrochloride (MP Biomedicals, Solon, Ohio).

*Salmonella enterica* serovar Typhimurium (ATCC 14028) and *Escherichia coli* (ATCC 25922) were grown on Luria-Bertani (LB) agar (Becton, Dickinson and Company) or in LB broth at 37° C. Experiments involving these bacteria were performed using biosafety level 2 (BSL-2) laboratory procedures.

Reagents

Celecoxib was extracted and purified from Celebrex capsules (Amerisource Health, Malvern, Pa.) with ethyl acetate followed by recrystallization in a mixture of ethyl acetate and hexane. Rofecoxib was synthesized according the procedure of Prasit et al. Prasit et al., Bioorg. Med. Chem. Lett. 9, p. 1773-8 (1999). The celecoxib-based compound library consisted of compounds 1-21, as described in Examples 2-6. The identity and purity (>99%) of these synthetic compounds were verified by proton nuclear magnetic resonance spectroscopy (300 MHz), high resolution mass spectrometry, and elemental analysis.

Macrophages

The RAW264.7 murine macrophage cell line and THP-1 human monocytic leukemia cell line were obtained from American Type Culture Collection (ATCC; Manassas, Va.). The RAW264.7 cells were maintained in Dulbecco's Modified Eagle's Medium (DMEM) (GIBCO-BRL, Invitrogen Corp., Carlsbad, Calif.) supplemented with 10% FBS (GIBCO-BRL). The THP-1 cells were maintained in RPMI 1640 containing 10% FBS. THP-1 cells were differentiated by treatment with 20 nM of 12-O-tetradecanoylphorbol 13-acetate (TPA) (Sigma-Aldrich, St. Louis, Mo.) for 48 h. All culture of murine and human cells was performed at 37° C. in a humidified incubator containing 5% CO2. Cells were seeded into 96- or 12-well tissue culture plates, and incubated for 8-12 hours prior to experimentation.

Antibacterial Assays

The minimum inhibitory concentration (MIC) of individual agents was determined by a broth microdilution method as described below. MIC was defined as the lowest concentration that significantly inhibited the bacterial growth. *F. tularensis* cells grown overnight on a chocolate II agar plate were suspended in PBS to an O.D. of 1.0 at 600 nm, which was equivalent to $10^{10}$ CFU/ml, and then diluted in modified TSB to a final concentration of $10^4$ CFU/ml. The bacterial suspension was exposed to the test agent at escalating doses, ranging from 1-64 µg/ml, in triplicate in 96-well plates, and incubated at 37° C. for 24 h (*F. novicida* and Schu S4) or 48 h (LVS). The MIC was derived from the concentration that exhibited no visible growth of bacteria. Subsequently, to analyze the viability of *F. novicida* and LVS after drug exposure, 100 µl of bacterial suspension from each well was serially diluted with PBS and spread onto chocolate II agar plates. After 24 h (*F. novicida*) or 48 h (LVS) of incubation at 37° C., the number of bacterial colonies on each plate was counted and expressed as CFU/ml. The effects of test agents on the growth of two additional Gram-negative bacteria, *S. enterica* serovar Typhimurium and *E. coli*, in LB broth or modified TSB were assayed as described above for *Francisella* spp.

Macrophage Viability Assay

The effect of individual agents on macrophage viability was assessed by using the 3-(4,5-dimethylthiazol-2-yl)-2,5-diphenyltetrazolium (MTT) assay. Jeffrey, M. E., Methods in Cell Science, 11(1), p. 3 (1988). RAW264.7 cells were seeded into 96-well plates at $2.5 \times 10^4$ cells/well (minimum of six wells per test group) in Dulbecco's Modified Eagle's Medium (DMEM) supplemented with 10% fetal bovine serum (FBS) and 10 µg/ml of gentamicin, and then incubated overnight at 37° C. in a humidified incubator containing 5% $CO_2$. The medium from each well was removed and replaced with fresh 5% FBS-supplemented DMEM containing various concentrations of test agents dissolved in DMSO (final concentration of 0.1%). Controls received DMSO alone at a concentration equal to that in drug-treated cells. After 8 h of treatment, the medium was removed, replaced by 200 µl of 0.5 mg/ml of MTT in 10% FBS-containing medium, and the cells were incubated in the $CO_2$ incubator at 37° C. for 1 h. Supernatants were removed from the wells, and the reduced MTT dye was solubilized in 200 µl/well of DMSO. Absorbances at 570 nm were determined on a plate reader. The viability of drug-treated cells was calculated as a percentage of vehicle-treated control cells, and an $IC_{50}$ for cell viability was determined by using CalcuSyn software (Biosoft, Cambridge, UK).

Assay for Intracellular Survival of *Francisella* in Macrophages

*F. novicida* cells grown overnight on a chocolate II agar plate were suspended in PBS to a concentration of approximately $10^{10}$ CFU/ml (as estimated by an O.D. of 1.0 at 600 nm). RAW264.7 murine macrophages and TPA-differentiated THP-1 cells were seeded into 12-well plates at $5 \times 10^5$ cells/well, and *F. novicida* was added at an MOI of 50. Mohaptra et al., Infect. Immun. 76, p. 3690-9 (2008). After centrifugation of plates at 800×g for 15 min to facilitate infection, macrophages were incubated at 37° C. in a humidified incubator containing 5% $CO_2$ for 2 h, exposed to 50 µg/ml of gentamicin for 30 min, and washed with pre-warmed PBS twice to remove killed extracellular bacteria. Mariathasan et al., J. Exp. Med. 202, p. 1043-9 (2005). Infected macrophages were then treated in triplicate with various concentrations of test agents for 8 h, after which culture medium was collected from each well and macrophages lysed with 500 µl of 0.1% sodium deoxycholate in PBS at 37° C. for 5 min to release intracellular bacteria. Mohaptra et al., Infect. Immun., 75, p. 390-6 (2007). Bacteria present in the collected culture medium, either as free bacteria or within floating macrophages, were harvested by centrifugation at 16,000×g for 5 min, followed by resuspension of the pellet in 500 µl of 0.1% sodium deoxycholate in PBS. Combined lysates were serially diluted with PBS and spread onto chocolate II agar plates. CFU were calculated after incubation for 24 h at 37° C. Survival of intracellular bacteria in drug-treated macrophages was calculated as a percentage of control (untreated) cells.

Statistical Analysis

Data are expressed as means±SD. Group means were compared using a two-tailed t-test for independent samples. Differences were considered significant at P<0.05. Statistical analyses were performed using SPSS for Windows (Version 16.0; SPSS, Inc. Chicago, Ill.).

Results

Differential Effect of Celecoxib and Rofecoxib on Inhibiting the Growth of *F. Tularensis* in Broth Culture.

As part of the inventors' effort to identify lead agents with antibacterial activity against *F. tularensis*, the effect of a panel of pharmaceuticals in clinical use on the growth of *F. novicida* and LVS in modified tryptic soy broth (TSB) was examined. Of the drugs examined, the cyclooxygenase-2 (COX-2) inhibitor celecoxib exhibited a significant ability to inhibit bacterial growth with MIC values of 32 μg/ml and 16 μg/ml for *F. novicida* and LVS, respectively (FIG. 1). As shown, treatment of these bacteria with celecoxib at the respective MICs led to a ≥log decrease in CFU, and bacteria were completely eliminated at 64 μg/ml and 32 μg/ml, respectively (FIG. 1B). Importantly, celecoxib was equipotent in suppressing the growth of the human virulent type A strain of *F. tularensis* Schu S4 with an MIC of 16 μg/ml (FIG. 1C). Moreover, this suppressive effect was highly specific against *Francisella* since celecoxib was inactive against two other gram-negative bacteria examined, namely *S. enterica* serovar Typhimurium and *E. coli*. In contrast, rofecoxib, a structurally distinct but more potent COX-2 inhibitor, had no appreciable effect on any of the bacteria examined at 64 μg/ml (FIGS. 1B and C), indicating that the antibacterial effect of celecoxib was attributable to an "off-target" mechanism independent of inhibiting a putative "COX-2-like" enzyme in *Francisella*.

Pharmacological Exploitation of the Anti-Francisella Activity of Celecoxib.

It was determined that the findings of an "off-target" antibacterial activity of celecoxib against *F. tularensis* could be exploited by using celecoxib as a molecular platform to develop additional potent anti-Francisella agents for therapeutic use. Accordingly, a focused compound library consisting of twenty-one celecoxib derivatives was established by replacing the methylphenyl ($R_1$) and sulfonamide ($R_2$) fragments of celecoxib with various functionalities. The MICs of these compounds for bacterial growth inhibition were measured following growth in modified TSB after 24 h (for *F. novicida*) or 48 h (for LVS) at 37° C., as shown in FIG. 2. Of them, compounds 2, 11, 12, 16, and 20 exhibited MICs of no greater than 4 μg/ml for both strains. In particular, compound 12 was able to suppress the growth of *F. novicida* and LVS at 2 and 1 μg/ml, respectively. This multifold increase in antibacterial activity showed that celecoxib could be structurally optimized to develop potent anti-Francisella agents.

Differential Cytotoxicity of Lead Agents for Macrophages.

Figure 3:
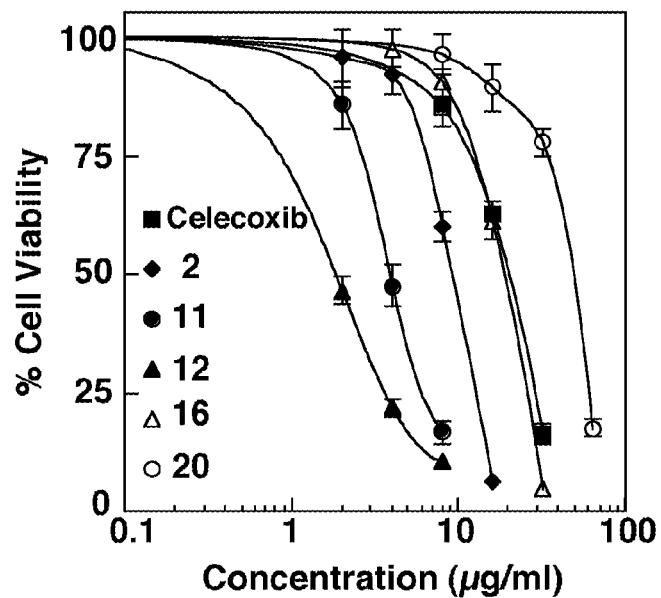
FIG. 3 shows the effect of celecoxib and its derivatives on RAW264.7 murine macrophage cells, with section (A) providing a graph showing the results of a cytotoxicity assay of selected agents, where RAW264.7 cells were treated with different doses of celecoxib and compounds (2, 11, 12, 16 and 20) in DMEM supplemented with 5% FBS for 8 h. The viability of drug-treated cells was measured using the MTT cell viability assay and expressed as a percentage of vehicle control (DMSO)-treated cells. Points, mean; bars, ±SD (n=3), and section (B) providing a table showing comparison of cytotoxicity and antimicrobial efficacy of selected agents.

Since the primary in vivo target for *F. tularensis* is the macrophage, the cytotoxicity of celecoxib and these lead agents was further assessed in RAW264.7 murine macrophage cells. FIG. 3A depicts the dose-response effects of individual agents on the death of RAW264.7 cells in 5% FBS-containing DMEM medium after 8-h treatment, of which the relative potency is in the order of 12>11>2>16>celecoxib>20. Serum was an important variable in this assay as prior studies had shown that serum can suppress the activity of these agents.

Although compound 12 at 2 μg/ml was highly effective in inhibiting bacterial growth, it also showed cytotoxicity for macrophages at the same concentration, i.e., $IC_{50}$/MIC ratio of 1.2 (FIG. 3B). On the other hand, compound 20 exhibited the highest $IC_{50}$/MIC ratio of 11.5, indicating a desirable selectivity in drug-induced bacterial growth inhibition relative to cytotoxicity for host cells. Moreover, like celecoxib, the inhibitory activity of compound 20 was specific for *Francisella* as it was inactive against the gram-negative bacteria *S. enterica* serovar Typhimurium and *E. coli* (data not shown).

The 50% inhibitory concentration ($IC_{50}$) of each agent tested from three independent experiments was calculated by using CalcuSyn software. The ratio of the MIC (bacteria growth inhibition) to the $IC_{50}$ (cell toxicity) for each agent was also calculated and served as an index of selectivity for antimicrobial activity relative to a cytotoxic effect (the higher the number the greater the selectivity).

Figure 4:
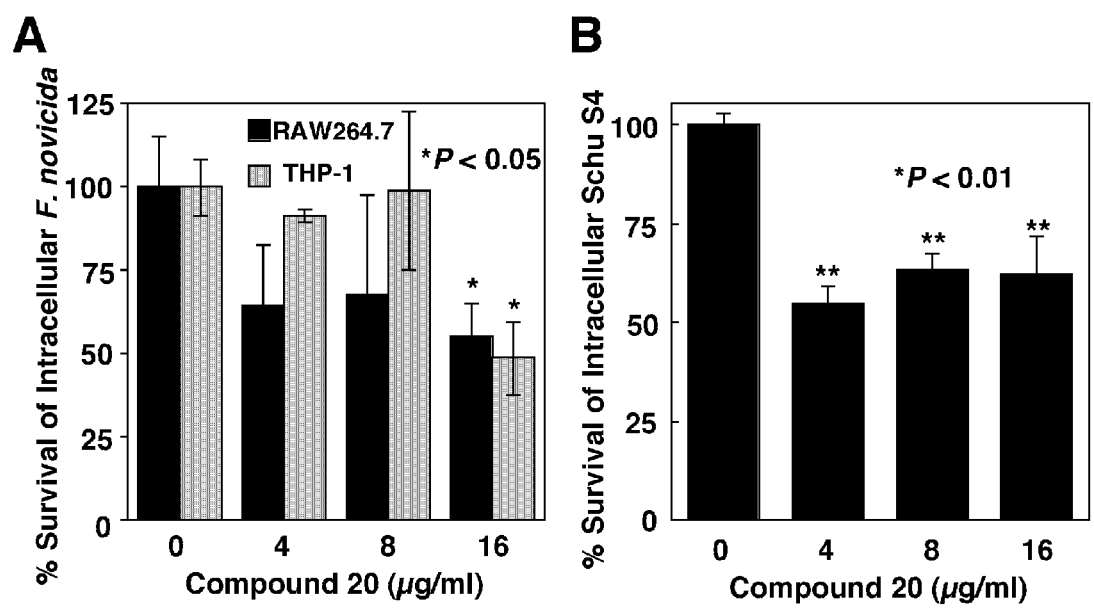
FIG. 4 shows the inhibition of intracellular *F. tularensis* by compound 20, with section (A) providing a bar graph showing that compound 20 decreased the survival of intracellular *F. novicida* in RAW264.7 and THP-1 cells, and section (B) showing the decrease of intracellular survival of *F. tualrensis* (type A, Schu S4) in THP-1 cells by compound 20. Data are presented as the % survival relative to vehicle control (DMSO)-treated cells. Columns, mean; bars, ±SD (n=3). *P<0.05.

Compound 20 inhibits the growth of intracellular *F. tularensis* in murine and human macrophages. Based on these results, compound 20 was further studied for its effect on inhibiting the intracellular survival of *F. novicida* in murine RAW264.7 and 12-O-tetradecanoyl-phorbol-13-acetate (TPA)-differentiated human THP-1 macrophages. After infection and removal of extracellular bacteria, infected macrophages were treated with 4, 8 and 16 ng/ml of compound 20 in 5% FBS-containing DMEM medium for 8 h. Intracellular bacteria were then harvested and enumerated by calculating CFU after growth on agar. As shown in FIG. 4A, compound 20 effectively inhibits intracellular *F. novicida* at 16 μg/ml ($P<0.05$). Subsequently, the effect of compound 20 on intracellular *F. tularensis* (type A, Schu S4) in TPA-treated THP-1 cells was assayed. At 4 μg/ml, compound 20 already showed significant inhibitory effect on the intracellular Schu S4 ($P<0.01$), indicating the higher susceptibility of Schu S4 to compound 20 than *F. novicida* (FIG. 4B).

Discussion

Several drugs that originally were not developed for the treatment of bacterial infections have been demonstrated to possess antimicrobial activity in vitro. For example, the cholesterol-lowering drug, statin, was shown to inhibit the in vitro growth of *Staphylococcus aureus*. Jerwood et al., J. Antimicrob. Chemother. 61, p. 362-4 (2008). The results provided herein demonstrated that celecoxib, a broadly used anti-inflammatory agent, exhibits an "off-target" antibacterial activity against *F. tularensis* in vitro. It is particularly noteworthy that the antimicrobial activity of celecoxib against *F. tularensis* is more potent than against *F. novicida*. This differential effect is reflected in the disparate MICs for *F. novicida* versus *F. tularensis* (type A Schu S4) and LVS. Moreover, the assessment of the anti-Francisella activity of new celecoxib derivatives revealed that *F. novicida* and LVS show a marked difference in their susceptibilities to celecoxib and its derivatives, especially compound 17, which had no measurable inhibitory effect on *F. novicida*, but was a potent inhibitor of LVS growth in modified TSB (FIG. 2). This finding indicates that the interaction between the drug and its putative bacterial target protein differs between *Francisella* spp. A possibility is that the binding site for celecoxib on its putative target protein differs, leading to higher binding affinity in *F. tularensis* strains, and stronger growth inhibition in vitro.

Among the celecoxib derivatives synthesized and evaluated, compound 20 was identified as having the best selectivity for its bacterial growth inhibitory effects relative to its cytotoxicity for macrophages. Equally important, it could inhibit the survival of intracellular *Francisella* in both murine and human macrophages although at a higher concentration than the MIC for bacteria grown in broth culture (16 μg/ml versus 4 μg/ml). This discrepancy reflects many factors that limit the access of antibacterial agents to intracellular pathogens, including serum protein binding and physical barriers imposed by biological membranes.

Because *Francisella* is primarily located in macrophages of the infected host, methods for targeted drug delivery to macrophages should be considered in the development of next generation anti-Francisella agents. For instance, strategies that couple compound 20 with a carrier that can be actively phagocytosed by macrophages may prove to be a promising means to attain both increased intracellular drug concentrations and specificity of drug delivery. One possible approach in this regard is to utilize the mannose receptor that is expressed abundantly on macrophages, which has been broadly used to enhance the specific delivery of drugs, oligonucleotides and proteins to intracellular compartments in macrophages. Irache et al., Expert Opin. Drug Deliv., 5, p. 703-24 (2008).

Celecoxib and rofecoxib are potent COX-2 inhibitors that have been shown to interact with the same binding pocket of the COX-2 enzyme with $IC_{50}$ values in the sub-μM range. Nonetheless, the data show that only celecoxib possessed antimicrobial activity toward *Francisella*, and that the MIC of celecoxib for *Francisella* growth inhibition (32 μg/ml) is much higher than its reported $IC_{50}$ for COX-2 inhibition (0.21 μg/ml) Prasit et al., Bioorg. Med. Chem. Lett., 9, p. 1773-8 (1999). These findings suggest that the antimicrobial activity of celecoxib is independent of the structural features that dictate its binding to COX-2. Thus, it appears likely that the putative bacterial target of celecoxib in *F. tularensis* is structurally distinct from the COX-2 enzyme. In addition to COX-2, celecoxib has been reported to possess inhibitory activity against other mammalian enzymes, including phosphoinositide-dependent kinase-1, carbonic anhydrase, sarcoplasmic/ER calcium ATPase (SERCA), and COX-1. Schonthal, A. H., Br. J. Cancer, 97, p. 1465-8 (2007). These mammalian enzymes may serve as leads to identify structurally similar bacterial proteins, of which one could be the putative antibacterial target of celecoxib in *F. tularesis*.

Accordingly, the protein sequences of these celecoxib-targeted enzymes were used to search for homologous protein sequences in the published proteome of *F. tularensis* (Schu S4), *F. novicida* and LVS at the National Center of Biotechnology Information (http://www.ncbi.nlm.nih.gov/). The results identified several proteins of *F. novicida* and LVS that share homology with carbonic anhydrase, SERCA and COX-1, which include superoxide dismutase, FGAM synthase and a cation transport ATPase (FTF1738c). These findings suggest that such an approach to identifying bacterial drug targets is feasible, and will facilitate the development of more potent and specific, celecoxib-derived anti-Francisella agents.

The complete disclosure of all patents, patent applications, and publications, and electronically available material cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

What is claimed is:

1. A method of treating infection by *Francisella tularensis* in a subject in need thereof by administering a therapeutically effective amount of a composition consisting of a compound selected from the group consisting of:
   4-(5-biphenyl-4-yl-3-trifluoromethyl-pyrazol-1-yl)-phenylamine;
   4-(5-naphthalen-1-yl-3-trifluoromethyl-pyrazol-1-yl)-phenylamine;
   4-[5-(6-methoxy-naphthalen-2-yl)-3-trifluormethyl-pyrazol-1-yl]-phenylamine; and
   4-[5-(4'-bromo-biphenyl-4-yl)-3-trifluoromethyl-pyrazolyl]-phenylamine;
   or a pharmaceutically acceptable salt thereof and optionally a pharmaceutically acceptable carrier.

2. The method of claim 1, wherein the compound is selected from the group consisting of:
   4-(5-biphenyl-4-yl-3-trifluoromethyl-pyrazol-1-yl)-phenylamine; and
   4-[5-(4'-bromo-biphenyl-4-yl)-3-trifluoromethyl-pyrazolyl]-phenylamine;
   and their pharmaceutically acceptable salts.

3. The method of claim 1, wherein the compound is 4-[5-(4'-bromo-biphenyl-4-yl)-3-trifluoromethyl-pyrazolyl]-phenylamine or a pharmaceutically acceptable salt thereof.

4. The method of claim 1, wherein the *Francisella tularensis* infection is inhibited in macrophage cells without significant toxicity to the macrophage cells.

5. The method of claim 1, wherein the *Francisella tularensis* is antibiotic resistant.

6. The method of claim 1, wherein the subject is a human.

* * * * *